United States Patent
Reddy et al.

(10) Patent No.: US 7,034,162 B2
(45) Date of Patent: Apr. 25, 2006

(54) AMORPHOUS FORM OF 3-[2-(DIMETHYLAMINO) ETHYL]-N-METHYL-1H-INDOLE-5-METHANE SULFONAMIDE SUCCINATE (SUMATRIPTAN SUCCINATE)

(75) Inventors: Manne Satyanarayana Reddy, Hyderabad (IN); Srinivasan Thirumalai Rajan, Hyderabad (IN); Mokkarala Suryanarayana Murthy, Hyderabad (IN); Achampeta Kodanda Ram Prasad, Hyderabad (IN)

(73) Assignees: Dr. Reddy's Laboratories Limited, Hyderabad (IN); Dr. Reddy's Laboratories, Inc., Upper Saddle River, NJ (US)

( * ) Notice: Subject to any disclaimer, the term of this patent is extended or adjusted under 35 U.S.C. 154(b) by 0 days.

(21) Appl. No.: 10/627,399

(22) Filed: Jul. 25, 2003

(65) Prior Publication Data

US 2004/0143002 A1    Jul. 22, 2004

(30) Foreign Application Priority Data

Aug. 12, 2000 (IN) .......................... 594/MAS/2002

(51) Int. Cl.
*C07D 209/10* (2006.01)
(52) U.S. Cl. ...................... 548/507; 574/415
(58) Field of Classification Search ................ 548/507; 574/415
See application file for complete search history.

(56) References Cited

U.S. PATENT DOCUMENTS 4,820,833 A * 4/1989 Crisp et al. ................. 540/220

OTHER PUBLICATIONS

Nicholas Cheronis, "Semimicro Experimental Organic Chemistry", 1958, Chapter 5.*
Winterbornet al., 1992, "composition", EP 0496307 A1.*

* cited by examiner

*Primary Examiner*—Taofiq Solola
*Assistant Examiner*—Robert Shiao
(74) *Attorney, Agent, or Firm*—Robert A. Franks; Milagros A. Cepeda; Edward D. Pergament

(57) ABSTRACT

The present invention relates to an amorphous form of Sumatriptan succinate of Formula (1). The present invention also relates to process for the preparation of an amorphous form of Sumatriptan succinate. The process for the preparation of an amorphous form of Sumatriptan succinate comprises refluxing an aqueous mixture of Sumatriptan or its succinate salt in alcoholic solvents such as methanol or nitrile solvents such as acetonitrile followed by evaporation of the solvent from the filtrate. The resulting residue is triturated with water immiscible aromatic or aliphatic hydrocarbon solvents such as cyclohexane to afford an amorphous form of Sumatriptan succinate.

16 Claims, 1 Drawing Sheet

Figure 1:
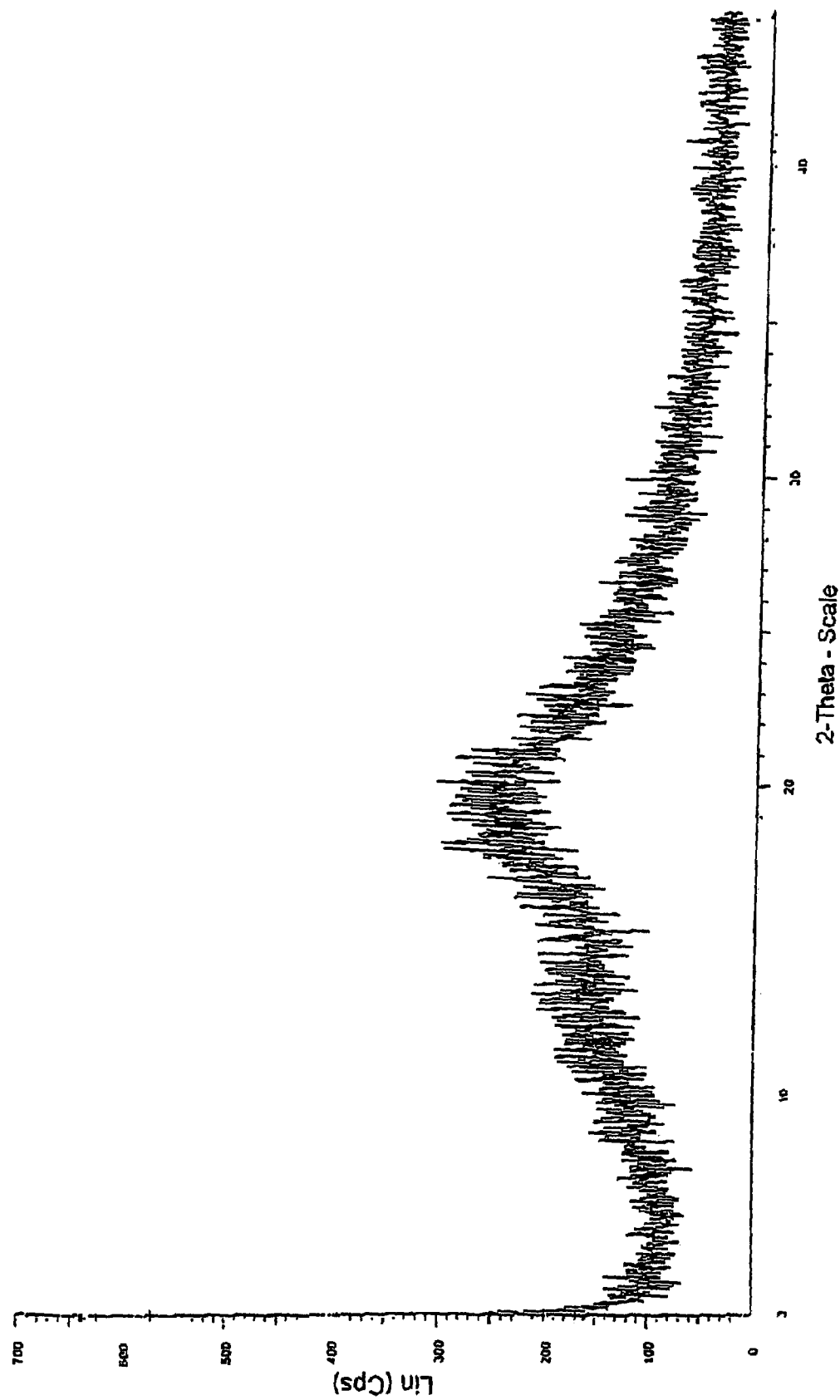

AMORPHOUS FORM OF 3-[2-(DIMETHYLAMINO) ETHYL]-N-METHYL-1H-INDOLE-5-METHANE SULFONAMIDE SUCCINATE (SUMATRIPTAN SUCCINATE)

FIELD OF THE INVENTION

The present invention relates to an amorphous form of 3-[2-(dimethylamino)ethyl]-N-methyl-1H-indole-5-methane sulfonamide succinate. It also relates to the process for the preparation of an amorphous form of 3-[2-(dimethylamino)ethyl]-N-methyl-1H-indole-5-methane sulfonamide succinate. The compound is generically known as Sumatriptan succinate, marketed under the name "Imitrex", which can be depicted as Formula (1).

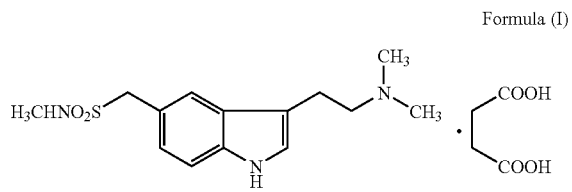

Formula (I)

Sumatriptan is an anti migraine compound, efficacious in the treatment of migraine. It has no significant effect on blood pressure, heart rate and no significant bronco constrictor effect on the lungs.

BACKGROUND OF THE INVENTION

Our co-pending Indian Patent application vide No.451/MAS/2002 disclosed the novel crystalline forms of Sumatriptan succinate, which are designated as Form-I and Form-II along with their process for preparation. These are also disclosed in PCT Application US03/19004 filed on Jun. 12, 2003.

Another co-pending Indian Patent application vide No.452/MAS/2002 described the purification process for obtaining highly pure Sumatriptan. A process for obtaining highly pure sumatriptan is also disclosed in PCT Application US03/19004 filed on Jun. 12, 2003.

It has been disclosed earlier that the amorphous forms in a number of drugs exhibit different dissolution characteristics and in some cases different bioavailability patterns compared to crystalline forms. For some therapeutic indications one bioavailability pattern may be favored over another. An amorphous form of Cefuroxime axetil is a good example for exhibiting higher bioavailability than the crystalline form. During our laboratory experimentation as a part of process development, an amorphous form of Sumatriptan succinate resulted while crystallizing the Sumatriptan in different solvents.

The present invention provides an amorphous form of Sumatriptan succinate. The invention also provides a process for the preparation of an amorphous form of Sumatriptan succinate.

The amorphous form of Sumatriptan succinate of the present invention is characterized by X-ray powder diffractogram, having broad peaks.

The amorphous form of Sumatriptan obtained in the present invention is free flowing, non-hydrated, non-solvated and thermally stable solid.

The process for the preparation of the amorphous form of the present invention is simple, eco-friendly and easily scalable.

U.S. Pat. Nos. 4,816,470; and 5,037,845 are related to the present field of the invention and both of these patents are hereby incorporated by reference in their entirety.

SUMMARY OF THE INVENTION

The present invention relates to an amorphous form of Sumatriptan succinate. The present invention also relates to a process for the preparation of amorphous form of Sumatriptan succinate. The process for the preparation of the amorphous form of Sumatriptan succinate comprises refluxing an aqueous mixture of Sumatriptan or its succinate salt in alcoholic solvents such as methanol or nitrile solvents such as acetonitrile followed by evaporation of the solvent from the filtrate. The resulting residue is triturated with water immiscible aromatic or aliphatic hydrocarbon solvents such as cyclohexane to afford an amorphous form of Sumatriptan succinate.

BRIEF DESCRIPTION OF THE ACCOMPANYING DRAWINGS

FIG. 1 is a characteristic X-ray powder diffraction pattern of a sample of an amorphous form of Sumatriptan succinate of the invention.

DETAILED DESCRIPTION OF THE INVENTION

The present invention relates to the novel amorphous form of Sumatriptan succinate and a process for the preparation thereof.

The present invention of an amorphous form of Sumatriptan succinate is characterized by X-ray powder diffractogram. The X-ray powder diffraction pattern of the amorphous form of Sumatriptan succinate is measured on a Bruker Axs, D8 Advance Powder X-ray Diffractometer with Cu K alpha-1 Radiation source.

The amorphous form of Sumatriptan succinate of the present invention has an X-ray powder diffractogram pattern is substantially as depicted in FIG. (1).

Another aspect of the present invention is a process for the preparation of an amorphous form of 3-[2-(Dimethylamino) ethyl]-N-Methyl-1H-indole-5-methane sulfonamide succinate (Sumatriptan succinate), which comprises, a) refluxing the aqueous mixture of Sumatriptan or its succinate salt in $C_1$–$C_5$ straight or branched chain alcoholic solvents selected from the group of methanol, ethanol, n-propanol, isopropanol, n-butanol, 2-butanol, 2-pentanol, preferably methanol or in nitrile solvents comprising of acetonitrile and propionitrile, preferably acetonitrile;

b) adding the succinate acid in case of Sumatriptan as a starting material in step (a);

c) filtering the reaction mixture obtained in either step (a) or step (b);

d) distilling off the solvent from the filtrate obtained in step (c);

e) adding water immiscible aliphatic or alicyclic hydrocarbon solvents comprising of petroleum ether, hexane, cyclohexane, heptane preferably cyclohexane to the residue obtained in step (d);

f) stirring the mass obtained in step (e) till the material separation completes;

g) filtering the solid obtained in step (f) by conventional methods;

h) drying the compound obtained in step (g) at a temperature of 30–50° C., preferably 25–35° C. under vacuum to afford the required novel amorphous form of Sumatriptan succinate.

The crystalline Form-I or Form-II of sumatriptan succinate can also be used in the above process to prepare the amorphous form.

The present inventive substance is non-hydrated, non-solvated, free flowing and thermally stable solid; hence it is well suited for pharmaceutical formulations.

Hence, the present invention is directed to provide an amorphous form of Sumatriptan succinate.

The process for the preparation of present invention is simple, eco-friendly and commercially viable.

The preparation of Sumatriptan or its pharmaceutical acceptable salts including succinate is known in the art.

The process for the preparation of crystalline Form-I and Form-II of Sumatriptan succinate was disclosed in our co-pending Indian patent application number vide No.451/MAS/2002.

The purification process for obtaining highly pure Sumatriptan was disclosed in our co-pending Indian Patent application vide No.452/MAS/2002.

Crystalline Form I and Form II of sumatriptan succinate and a process for obtaining highly pure sumatriptan are disclosed in PCT Application US03/19004 filed on Jun. 12, 2003.

The present invention is illustrated by the following examples, which are not intended to limit the effective scope of the claims.

Preparation of the Novel Amorphous Form of Sumatriptan Succinate:

EXAMPLE 1

Crystalline Form-I of Sumatriptan succinate (15.0 grams), water (75.0 ml) and methanol (150.0 ml) were heated to reflux temperature. The reaction mass was stirred for 15–30 minutes at reflux and filtered in hot condition. The solvent was distilled off completely from the filtrate under reduced pressure at a temperature of below 35–45° C. Cyclohexane (100 ml) was added to the resulting residual mass and stirred for 1–2 hours at a temperature of 25–35° C. to crystallize the solid. Then the solid was filtered, washed with cyclohexane (50 ml) and on subsequent drying under vacuum at a temperature of 25–35° C. resulted the amorphous form of Sumatriptan succinate of the invention.

(Weight: 12.5 grams, MC 0.5% w/w)

EXAMPLE 2

Crystalline Form-I of Sumatriptan succinate (15.0 grams), water (75.0 ml) and Acetonitrile (150.0 ml) were heated to reflux temperature. The reaction mass was stirred for 15–30 minutes at reflux and filtered in hot condition. The solvent was distilled off completely from the filtrate under reduced pressure at a temperature of below 35–45° C. Cyclohexane (100 ml) was added to the resulting residual mass and stirred for 1–2 hours at a temperature of 25–35° C. to crystallize the solid. Then the solid was filtered, washed with cyclohexane (50 ml) and on subsequent drying under vacuum at a temperature of 25–35° C. resulted the amorphous form of Sumatriptan succinate of the invention.

(Weight: 13.0 grams, MC 0.5% w/w)

EXAMPLE 3

Crystalline Form-II of Sumatriptan succinate (10.0 grams), water (50.0 ml) and methanol (100.0 ml) were heated to reflux temperature. The reaction mass was stirred for 15–30 minutes at reflux and filtered in hot condition. The solvent was distilled off completely from the filtrate under reduced pressure at a temperature of below 35–45° C. Cyclohexane (100 ml) was added to the resulting residual mass and stirred for 1–2 hours at a temperature of 25–35° C. to crystallize the solid. Then the solid was filtered, washed with cyclohexane (50 ml) and on subsequent drying under vacuum at a temperature of 25–35° C. there resulted the amorphous form of Sumatriptan succinate of the invention.

(Weight: 9.3 grams, MC 0.6% w/w)

EXAMPLE 4

Crystalline Form-II of Sumatriptan succinate (15.0 grams), water (75.0 ml) and acetonitrile (150.0 ml) were heated to reflux temperature. The reaction mass was stirred for 15–30 minutes at reflux and filtered in hot condition. The solvent was distilled off completely from the filtrate under reduced pressure at a temperature of below 35–45° C. Cyclohexane (100 ml) was added to the resulting residual mass and stirred for 1–2 hours at a temperature of 25–35° C. to crystallize the solid. Then the solid was filtered, washed with cyclohexane (50 ml) and on subsequent drying under vacuum at a temperature of 25–35° C. there resulted the amorphous form of Sumatriptan succinate of the invention.

(Weight: 9.5 grams, MC 0.8% w/w)

EXAMPLE 5

Sumatriptan (10.0 grams), water (50.0 ml), succinic acid (3.99 grams) and acetonitrile (100.0 ml) were heated to reflux temperature. The reaction mass was stirred for 15–30 minutes at reflux and filtered in hot condition. The solvent was distilled off completely from the filtrate under reduced pressure at a temperature of below 35–45° C. Cyclohexane (100 ml) was added to the resulting residual mass and stirred for 1–2 hours at a temperature of 25–35° C. to crystallize the solid. Then the solid was filtered, washed with cyclohexane (50 ml) and on subsequent drying under vacuum at a temperature of 25–35° C. there resulted the amorphous form of Sumatriptan succinate of the invention.

(Weight: 12.0 grams, MC 0.7% w/w)

The Sumatriptan succinate obtained from the above examples had similar XRD patterns, which showed a plain halo with no peaks indicating the amorphous nature, of the material.

Detailed Description of the Accompanying Drawing

FIG. 1 is characteristic X-ray powder diffraction pattern of a sample of an amorphous form of Sumatriptan succinate of the invention.

Vertical axis: Intensity (CPS); Horizontal axis: 2 Theta (degrees).

It shows a plain halo with no peaks, which is characteristic of the amorphous nature of the product.

We claim:

1. A process for the preparation of an amorphous form of 3-[2-(dimethylamino) ethyl]-N-methyl-1H-indole-5-methane sulfonamide succinate (Sumatriptan succinate), which comprises:
   a) heating to reflux an aqueous mixture of Sumatriptan in a $C_1$–$C_5$ straight or branched chain alcoholic solvent or in a nitrile solvent of formula RCN, wherein R is a $C_1$–$C_5$ alkyl group;
   b) adding succinic acid to the mixture in step a); and
   c) adding a water immiscible aliphatic or alicyclic hydrocarbon solvent to the mixture in step b).

2. A process for the preparation of an amorphous form of 3-[2-(dimethylamino)ethyl]-N-methyl-1H-indole-5-methane sulfonamide succinate (Sumatriptan succinate) which comprises:
   a) heating to reflux an aqueous mixture of Sumatriptan succinate in a $C_1$–$C_5$ straight or branched chain alcoholic solvent; and
   b) adding a water immiscible aliphatic or alicyclic hydrocarbon solvent to the mixture in step a).

3. The process according to claim 1, wherein the Sumatriptan succinate in step a) is crystalline.

4. The process according to claim 2, wherein the Sumatriptan succinate in step a) is crystalline.

5. The process according to claim 1, wherein the straight or branched chain alcoholic solvent is selected from the group consisting of methanol, ethanol, n-propanol, iso-propanol, n-butanol, 2-butanol, and 2-pentanol.

6. The process according to claim 2, wherein the straight or branched chain alcoholic solvent is selected from the group consisting of methanol, ethanol, n-propanol, iso-propanol, n-butanol, 2-butanol, and 2-pentanol.

7. The process according to claim 1, wherein the nitrile solvent is selected from the group consisting of acetonitrile, propionitrile, and mixtures thereof.

8. The process according to claim 2, wherein the nitrile solvent is selected from the group consisting of acetonitrile, propionitrile, and mixtures thereof.

9. The process according to claim 5, wherein the alcoholic solvent is methanol.

10. The process according to claim 6, wherein the alcoholic solvent is methanol.

11. The process according to claim 7, wherein the nitrile solvent is acetonitrile.

12. The process according to claim 8, wherein the nitrile solvent is acetonitrile.

13. The process according to claim 1, wherein the water immiscible aliphatic or alicyclic hydrocarbon solvent is selected from the group consisting of petroleum ether, hexane, cyclohexane, heptane, and mixtures thereof.

14. The process according to claim 2, wherein the water immiscible aliphatic or alicyclic hydrocarbon solvent is selected from the group consisting of petroleum ether, hexane, cyclohexane, heptane, and mixtures thereof.

15. The process according to claim 13, wherein the water immiscible aliphatic or alicyclic hydrocarbon solvent is cyclohexane.

16. The process according to claim 14, wherein the water immiscible aliphatic or alicyclic hydrocarbon solvent is cyclohexane.

* * * * *